US006344322B1

(12) United States Patent
Polyak et al.

(10) Patent No.: US 6,344,322 B1
(45) Date of Patent: Feb. 5, 2002

(54) SUBTLE MITOCHONDRIAL MUTATIONS AS TUMOR MARKERS

(75) Inventors: Kornelia Polyak, Brookline, MA (US); Bert Vogelstein, Baltimore; Kenneth W. Kinzler, BelAir, both of MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/377,856

(22) Filed: Aug. 20, 1999

Related U.S. Application Data

(60) Provisional application No. 60/097,307, filed on Aug. 20, 1998.

(51) Int. Cl.[7] .......................... C12Q 1/68; C07H 21/64; C12P 19/34; C12N 5/08
(52) U.S. Cl. ..................... 435/6; 435/91.1; 435/91.2; 435/366; 536/23.1; 536/24.33; 536/24.3
(58) Field of Search .......................... 435/6, 91.2, 366, 435/91.1, 71, 72, 5; 536/23, 24.3, 24.33; 514/44, 12; 436/504

(56) References Cited

U.S. PATENT DOCUMENTS

| 5,683,877 A | * | 11/1997 | Lu-Chang et al. | ............. 435/6 |
| 5,879,890 A | * | 3/1999 | Laken et al. | .................. 435/6 |
| 5,935,787 A | * | 8/1999 | Sidransky | ..................... 435/6 |
| 6,025,127 A | * | 2/2000 | Sidransky | ..................... 435/6 |

OTHER PUBLICATIONS

Alonso et al. Detection of somatic mutations in the mitochondrial DNA control region of colorectal and gastric tumors by heteroduplex and single–strand conformation analysis. Electrophoresis vol. 18, pp. 682–685, May 1997.*
Chee et al. Accessing Genetic information with high density DNA arrays. Science, vol. 274, pp. 610–614, Oct. 1996.*
Hopgood et al. "Strategies for Automated Sequencing of Human Mitochondrial DNA Directly from PCR Products" Biotechniques, vol. 13, No. 1, pp. 82–92 (1992).
Ivanova et al. "Mitochondrial DNA Sequence Variation in Human Leukemic Cells" In J. Cancer: 76 495–498 (1998).
Alonso et al. "Detection of somatic mutations in the mitochondrial DNA control region of colorectal and gastric tumors by heteroduplex and single–strand conformation analysis" Electrophoresis, vol 18 (5) pp. 682–5 (1997).
Khrapko et al. Proc. Natl. Acad. Sci. USA, vol. 94, pp. 13798–13803, Dec. 1997.
Casali et al. "Mitochondrial G8363 A mutation presenting as cerebellar ataxia and lipomas in an Italian family" Neurology—American academy of Neurology, vol. 52 (5) pp. 1103–Mar. 4, 1999.
Tanaka et al. "Automated Sequencing of Mitochondrial DNA" Methods in Enzymology, vol. 264, pp. 407–21 (1996).
Taira et al. "Tumor–associated mutations of rat mitochondrial transfer RNA genes" Nucleic Acids Research, vol. 11 (6), pp. 1635–43 (1983).

Ladanyi et al. "Analysis of nuclear and mitochondrial DNA alterations in thyroid and renal oncocytic tumors" Cytogenet Cell Genet 66:253–259 (1994).
Burgart e tal. "Somatic Mitochondrial Mutation in Gastric Cancer" American Journal fo Pathology, vol. 147, No. 4 Oct. 1995 pp. 1105–1111.
Wallace "Mitochondrial DNA sequence variation in human evolution and disease" Proc. Natl. Acad. Sci USA vol. 91, pp. 8739–8749 Sep. 1994.
Corral et al. "RNAs containing mitochondrial ND6 and CO1 sequences present an abnormal structure in chemically induced rat hepatomas" Nucleic Acids Research, vol. 17 (13) pp. 5191–5206.
Heerdt et al. "Polymorphisms, but Lack of Mutations or Instability, in the Promoter Region of the Mitochondrial Genome in Human Colonic Tumors" Cancer Research 54, 3912–3915 Jul. 15, 1994 pp. 3912–3915.
Yamamoto et al. "Significant Existence of Deleted Mitochondrial DNA in Cirrhotic Liver Surrounding Hepatic Tumor" Biochemical and Biophysical Research Communications, vol. 182, No. 2, pp. 913–920 Jan. 31, 1992.
Wallace "Mitochondrial Diseases in Man and Mouse" Science, vol. 283, Mar. 5, 1999, pp. 1482–1488.
Welter et al. "Alteration of Mitochondrial DNA in Human Oncocytomas" Genes, Chromosomes & Cancer 1:79–82 (1989).
Burgart et al. "Somatic mitochondrial mutation in gastric cancer" American Journal of Pathology, vol. 147, No. 4, 1995, pp. 1105–1111.
Welter et al. "Alteration of mitochondrial DNA in human oncocytomas" Genes, Chromosomes and Cancer, vol. 1, 1989 pp. 79–82.
Tallini et al. "Analysis fo nuclear and mitochondrial DNA alterations in thyroid and renal oncocytic tumors" Cytogenetics and Cell Genetics, vol. 66, 1994, pp. 253–259.
Yamamoto et al. "Significant existence of deleted mitochondrial DNA in cirrhotic liver surrounding hepatic tumor" Biochemical and biophysical research Communications, vol. 182, No. 2, 1992, pp. 913–920.
Kharpko et al. "Mitochondrial mutations spectra in human cells and tissues" Proceedings of the National Academy of Sciences USA, vol. 94, 1997, pp. 13798–13803.
D.C. Wallace "Mitochondrial DNA sequence variation in human evolution and disease" Proceedings of the National Academy of Sciences USA, vol. 91, 1994, pp. 8739–8746.
Ivanova et al. "Mitochondrial DNA sequence variation in human leukemic cells" International Journal of Cancer, vol. 76, 1998, pp. 495–498.
Nakamura et al. "A novel homoplasmic point mutation at mitochondria DNA (mtDNA) nucleotide 3308 in a family with a typical diabetes mellitus (ADM) of african americans (AA)" Diabetes, vol. 46, No. Supp, 1997, pp. 175A.

* cited by examiner

*Primary Examiner*—Stephanie W. Zitomer
*Assistant Examiner*—Cynthia Wilder
(74) *Attorney, Agent, or Firm*—Banner & Witcoff, Ltd.

(57) ABSTRACT

The accumulation of homoplasmic somatic mutations has been observed in the mitochondrial DNA of certain tumor cells. The presence or recurrence of a tumor can be detected by determining the presence of single basepair mutations in the mitochondrial genome from a cell sample of a patient.

27 Claims, 2 Drawing Sheets

SUBTLE MITOCHONDRIAL MUTATIONS AS TUMOR MARKERS

This application claims the priority of provisional U.S. application Ser. No. 60/097,307, filed Aug. 20, 1998.

The U.S. Government retains certain rights in this invention due to funding as provided by grant CA43460 awarded by the National Institutes of Health.

TECHNICAL FIELD OF THE INVENTION

The invention is related to the area of cancer genetics. In particular it is related to somatic mutations associated with cancer.

BACKGROUND OF THE INVENTION

The human mitochondrial genome is a 16 kilobase circular, double stranded DNA that encodes 13 polypeptides of the mitochondrial respiratory chain, 22 transfer RNAs, and two ribosomal RNAs required for protein synthesis. The mitochondrial genome is particularly susceptible to mutations because of the high level of reactive oxygen species generated in the organelle coupled with a low level of DNA repair (7–10). Surprisingly, there has been little detailed analysis of alterations in human mitochondrial DNA in cancer, although there are indications that mitochondria may be involved in neoplasia and apoptosis (2–6) as well as cancerous growth (1). Thus, there remains a need in the art to identify a correlation of alterations in human mitochondrial DNA with cancer.

SUMMARY OF THE INVENTION

It is an object of the invention to provide a method to aid in detecting the presence of tumor cells in a patient. This and other objects of the invention are provided by one or more of the embodiments described below.

One embodiment of the invention provides a method of screening patients for the presence of tumor cells. The method comprises a step for determining the presence of a single basepair mutation in a mitochondrial genome of a cell sample of a patient. If a single basepair substitution is found in a cell sample of the patient which is not in normal tissue of the patient, the patient is identified as having a tumor.

The invention thus provides the art with new methods of detecting and tracing tumors by examining mitochondrial DNA for the appearance of somatic mutations.

BRIEF DESCRIPTION OF THE DRAWINGS

FIG. 1 shows examples of mitochondrial DNA mutations. The sequence of the mitochondrial genome was determined in normal cells, primary tumors, and tumor cell lines from the same patients. Arrows indicate the G-to-A transition (antisense strand) at codon 121 of the COX subunit I gene in line V425, an A insertion within the (A)8 tract of the ND5 gene in line V425, a T-to-C transition at codon 1 of the ND1 gene in line 478, and a G-to-A transition (antisense strand) at codon 142 of the COX subunit II gene in line V429.

FIG. 2A to FIG. 2C depict somatic cell fusions. FIG. 2B. Analysis of the mitochondrial DNA utilizing the T-to-C variant at nucleotide 4,216 that creates a recognition site for Nla III (CATG). The C variant, giving rise to 376 and 231 fragments following restriction digest of a 1,140 bp PCR product, is present only in DLD-1 cells.

DETAILED DESCRIPTION OF THE INVENTION

The inventors have found that the presence of subtle mutations in the mitochondrial genome can be used as a means to trace the presence, spread, metastasis, growth, or recurrence of a tumor in a patient. Such subtle mutations include single basepair substitutions, single basepair insertions, and single basepair deletions. Single basepair substitutions can be either transitions or transversions, although the former are more frequent. Detection of such mutations can be useful to screen for the initial appearance of a tumor as well as the recurrence of a previously identified tumor. The methods are particularly suited to monitor anti-cancer therapy, recurrence, metastasis, and completeness of surgical removals.

A single basepair substitution is the substitution of a single nucleotide base with a different nucleotide base at the same position, with the corresponding substitution of the complementary base on the other strand of the DNA. While any single basepair substitution is conceivable within the scope of the invention, the most frequently encountered substitutions are those which are consistent with oxidative damage, such as T to C or G to A transitions. The mutations can appear in protein coding regions or in regions which encode ribosomal or transfer RNAs.

The homoplasmic property of most mutant mitochondrial genomes from tumors permits the ready detection of such mutations within a sample of mitochondrial DNA from a patient. Homoplasmic mutations are those which appear in essentially all of the copies of the mitochondrial genome within a given cell or tissue. However, heteroplasmic mutations, which are those appearing in only a fraction of the mitochondrial genomes of a cell or tissue, are also suitable for use with the invention.

Any cell sample can be tested from a patient who has cancer or is suspected of having cancer. Suitable cell samples include, but are not limited to, tissue from a growth suspected or known to be cancerous, tissue adjacent to a resection of a tumor, and tissue distant from the site of a tumor, such as lymph nodes which are suspected of bearing metastatic cells. Cells can also be obtained from bodily fluids or secretions, e.g., blood, urine, sputum, saliva, or feces, which may contain cancerous cells or metastatic cells. Cell samples can also be collected from other bodily secretions and tissues as is known in the art. A cell sample can be collected from suspected or known cancerous tissue or from bodily fluids or secretions harboring cancer cells as well as from suspected or known normal tissue or bodily fluids or secretions harboring normal cells.

In order to detect mutations of the mitochondrial genome from a cell sample of a patient, mitochondrial DNA can be isolated from the cell sample using any method known in the art. One way of identifying subtle mutations involves sequencing the mitochondrial DNA. This can be done according to any method known in the art. For example, isolated mitochondrial DNA can be cleaved using endonucleases into overlapping fragments of appropriate size for sequencing, e.g., about 1–3 kilobases in length, followed by polymerase chain reaction (PCR) amplification and sequencing of the fragments. Examples of DNA sequencing methods are found in Brumley, R. L. Jr., and Smith, L. M., 1991, Rapid DNA sequencing by horizontal ultrathin gel electrophoresis, *Nucleic Acids Res.* 19:4121–4126 and Luckey, J. A., Drossman, H., Kostihka, T.; and Smith, L. M., 1993, High-speed DNA sequencing by capillary gel electrophoresis, *Methods Enzymol.* 218:154–172. Amplification methods such as PCR can be applied to samples as small as a single cell and still yield sufficient DNA for complete sequence analysis. The combined use of PCR and sequencing of mitochondrial DNA is described in Hopgood, R., Sullivan, K. M., and Gill, P., 1992, Strategies for automated sequencing of human mitochondrial DNA directly from PCR products, *Biotechniques* 13:82–92 and Tanaka, M., Hayakawa, M., and Ozawa, T., 1996, Automated sequencing of mitochondrial DNA, *Methods Enzymol.* 264:407–21.

Mutations can first be identified by comparison to sequences present in public databases for human mitochondrial DNA, e.g., at http://www.gen.emory.edu/mitomap.html. Any single basepair substitution identified in the sample DNA compared to a normal sequence from a database can be confirmed as being a somatic mutation as opposed to a polymorphic variant by comparing the sample mitochondrial DNA or sequences obtained from it to control cell mitochondrial DNA from the same individual or sequences obtained from it. Control cells are isolated from other apparently normal tissues, i.e., tissues which are phenotypically normal and devoid of any visible, histological, or immunological characteristics of cancer tissue. A difference between the sample and the control identifies a somatic mutation which is associated with the tumor.

An alternative to serially sequencing the entire mitochondrial genome in order to identify a single basepair substitution is to use hybridization of the mitochondrial DNA to an array of oligonucleotides. Hybridization techniques are available in the art which can rapidly identify mutations by comparing the hybridization of the sample to matched and mismatched sequences which are based on the human mitochondrial genome. Such an array can be as simple as two oligonucleotide probes, one of whose sequence matches the wild-type or mutant region containing the single base substitution (matched probe) and another whose sequence includes a single mismatched base (mismatch control probe). If the sample DNA hybridizes to the matched probe but not the mismatched probe, it is identified as having the same sequence as the matched probe. Larger arrays containing thousands of such matched/mismatched pairs of probes on a glass slide or microchip ("microarrays" or "gene chips") are available which are capable of sequencing the entire mitochondrial genome very quickly. Such arrays are commercially available. Review articles describing the use of microarrays in genome and DNA sequence analysis and links to their commercial suppliers are available at www.gene-chips.com.

The invention can be used to screen patients suspected of having cancer for the presence of tumor cells. A cell sample is first obtained from a suspected tumor of the patient, or is obtained from another source such as blood or lymph tissue, for example, if metastasis is suspected. The cell sample is tested to determine the presence of a single basepair mutation in mitochondrial DNA from the cell sample using the techniques outlined above. Optionally, a cell sample from normal, non-cancerous cells or tissue of the patient is also obtained and is tested for the presence or absence of a single basepair mutation in mitochondrial DNA. If a single basepair mutation is determined which is not present in a cell sample from normal tissue of the patient, then the mutation is a somatic mutation and the presence of tumor cells in the patient is indicated. If one or more single basepair mutations are determined in the mitochondrial genome of the cell sample of the patient, then the patient is identified as having a tumor. As in any diagnostic technique for cancer, to confirm or extend the diagnosis, further diagnostic techniques may be warranted. For example, conventional histological examination of a biopsy specimen can be performed to detect the presence of tumor cells, or analysis of a tumor-specific antigen in a blood or tissue sample can be performed.

The method outlined above can be practiced either in the situation where the somatic mutation is previously known or previously unknown. Based on the inventors' findings, the identification of a previously unknown somatic mutation in a mitochondrial genome of a cell of a patient is likely to indicate the presence of tumor cells in the patient. Therefore, the method can be practiced even in the absence of prior knowledge about any particular somatic mutation. The method can also be carried out subsequent to the discovery of a somatic mutation in a mitochondrial genome of a cell of the patient or of another patient. In this case, a previous association of the somatic mutation with the presence of a tumor in the patient or in another patient strongly indicates the presence of tumor cells in the patient. It may also indicate the recurrence of a tumor or the incomplete prior removal of cancerous tissue from the patient.

The effectiveness of therapy can be evaluated when a tumor has already been identified and found to contain a single basepair substitution in the mitochondrial genome. Once a single basepair mutation has been identified in the mitochondrial DNA of a tumor of the patient, further tumor cells can be detected in tissue surrounding a resection or at other sites, if metastasis has occurred. Using the methods outlined above, the recurrence of the tumor or its incomplete removal can be assessed. Similarly, if a tumor has been treated using a non-surgical method such as chemotherapy or radiation, then the success of the therapy can be evaluated at later times by repeating the analysis. The step for determining the presence of a single basepair mutation in a mitochondrial genome of a cell sample of a patient can be performed 1, 2, 3, 4, 5, 6, 8, 10, or more times in order to monitor the development or regression of a tumor or to monitor the progress or lack of progress of therapy undertaken to eliminate the tumor.

Upon repeated analyses, the step for determining the presence of a single basepair mutation is simplified, because only a well defined and limited region of the genome need be sequenced. Using the hybridization method, for example, it is possible to evaluate the presence of the mutation with only a single matched/mismatched pair of oligonucleotide probes in the array. In the event that a mixture of genotypes is observed, it is possible to obtain quantitative information about the relative amount of each mitochondrial genotype using techniques known to the art, e.g., hybridization. Quantitative analysis can reveal changes in the relative proportion of tumor to normal cells in a tissue over time or in response to therapy.

The methods described above were used to study somatic mutations in mitochondrial DNA from human colorectal tumor cells (see Examples 1 and 2). The mutations observed generally were transitions, affecting G residues, which are the preferred targets for oxidative damage to DNA in general and mitochondrial DNA in particular (at least in vitro) (12, 13, 17, 18). This mutational spectrum supports the idea that the mitochondrial DNA mutations resulted from the reactive oxygen species continually generated in mitochondria. Sequence analyses of nuclear genes from the same ten cell lines studied for mitochondrial DNA mutations indicated that the prevalence of mutations is at least ten-fold higher in the mitochondrial genome than in the nuclear genome of those cells. Previous experiments have demonstrated large deletions in the mitochondrial DNA of some tumors (19–23), rather than the subtle mutations observed here. No deletions were observed in the cell lines studied here, despite several attempts to find them using multiple primer pairs in PCR-based strategies. The literature reveals no previous attempts to search for subtle mutations of mitochondrial genomes by complete sequencing.

The mutations reported in Table 1 were mostly homoplasmic, while the deletions previously observed in tumor cells or normal cells of aging individuals were generally heteroplasmic, present only in a small proportion of the mitochondrial population (19–24). The results presented here are not at variance with a previous study in which no somatic mutations in 200 bp of D-loop sequence were found. This D loop sequence contains promotor elements for transcription of the mitochondrial genome, while the mutations discovered by the inventors were confined to regions encoding mitochondrial proteins or rRNA.

The striking and unexpected homoplasmy of the mutations identified by the inventors indicates significant selection at several levels. First, the somatically mutant mitochondrial genome must be replicated better than that present in the germ-line. Previous experiments have indicated that replication of mitochondria can be controlled individually, in that signals from aberrantly functioning mitochondria induce their overreplication, perhaps in a compensating effort (25). The fusion experiments of Example 2 demonstrate that the process of mitochondrial selection in tumor cells can take place rapidly (FIG. 2C). Over the thousands of generations required for tumorigenesis in vivo, this process could easily result in the replacement of all mitochondrial genomes within the cell with a mutant form. This cell could then overtake the population through clonal growth, either because the aberrant mitochondria themselves endowed the cell with a selective growth advantage or because that cell sustained a nuclear gene mutation providing such an advantage.

This explanation invokes the idea that the mitochondrial mutations may themselves have a functional effect. It is unlikely that most of the observed somatic mutations result in major perturbations of mitochondrial function, as oxygen consumption and the respiratory chain enzymatic activities of several of the lines listed in Table 1 were largely normal. Instead, these mutations, perhaps in concert with polymorphic variations in mitochondrial DNA, probably result in subtle changes which might generate slightly higher levels of ROS. It has been shown that low levels of ROS are highly mitogenic, while high ROS levels are toxic (9). Regardless of the mechanism for their selection, however, the mutations that have been identified represent a previously unrecognized alteration in tumor cells that could have significant effects on the cellular processes controlled by mitochondria. Their homoplasmy raises fascinating questions about the control of mitochondrial DNA at the intramitochondrial, intracellular, and cellular population levels. It indicatea that a single cell with a mutant mitochondrial genome had acquired a selective growth advantage during tumor evolution, allowing it to become the predominant cell type within the tumor cell population. Furthermore, it is important to appreciate that cells, including the colorectal cancer cell lines used here, each contain hundreds of mitochondria, and each mitochondrion contains one to ten DNA molecules (14). The homoplasmy therefore additionally indicates that each mutant mitochondrial genome had a replicative advantage within the particular mitochondrion in which it occurred, and that this mitochondrion had selectively proliferated over other mitochondria in the same cell. Alterations of tumor mitochondrial DNA may also provide clues to their environmental or genetic background, a hypothesis that can be tested in the future using DNA chip technologies (26).

The above disclosure generally describes the present invention. A more complete understanding can be obtained by reference to the following specific examples, which are provided herein for purposes of illustration only and are not intended to limit the scope of the invention.

EXAMPLE 1

Identification of somatic mutations in mitochondrial DNA of human colorectal cancer cells.

To determine whether mutations of the mitochondrial DNA were present in human colorectal tumors, the entire mitochondrial genome was PCR-amplified from ten human colorectal cancer cell lines in 1–3 kb overlapping fragments and the PCR products completely sequenced. The use of large PCR products excluded the possibility that nuclear pseudogenes would complicate this analysis (11).

Cell lines and tumors. Derivation and maintenance of the VACO lines has been previously described (27). The DLD-1, HCT116, SW837 and HT29 human colorectal cancer cell lines were obtained from ATCC and maintained in McCoy's medium (Gibco, BRL) supplemented with 10% fetal bovine serum (Hyclone) and antibiotics (Gibco, BRL).

DNA purification, PCR amplification and sequencing. Cellular DNA from cell lines, from primary tumors, and from normal colonic mucosa was isolated as previously described (28). Overlapping fragments (1–3 kb each) of the mitochondrial genome were amplified by PCR using this DNA as template. The sequencing method allowed the detection of any mutation present in >25% of the mitochondrial DNA molecules within a given sample. In selected cases, the validity of the sequence data was confirmed using purified mitochondrial DNA as templates. To confirm the mutations in the primary tumors, smaller PCR fragments were generated from the DNA purified from microdissected, paraffin-embedded samples. Manual sequencing of the DNA fragments was performed using Thermosequenase (Amersham) and a Genomyx electrophoresis apparatus (Beckman).

Sequence analysis. The sequences obtained were first compared to those recorded in the mitochondrial databank at www.gen.emory.edu/mitomap.html. Eighty-eight sequence variants were identified (4–31 per tumor) that were not recorded in this databank. These included 27 variants which were predicted to alter the amino acid sequence of the encoded protein, 48 variants which were in protein coding regions but predicted to be silent, and 13 which affected rRNA or tRNA genes.

The database search provided only preliminary evidence for mutations, however, as it could not distinguish somatic mutations from rare germ-line variants. To make this distinction, mitochondrial DNA sequences were determined from normal colons from the same patient. This analysis showed that at least seven of the lines contained true somatic mutations. Three of the lines contained a single mutation, while four others contained two or three mutations (Table 1).

Each of the 27 sequence variants predicted to result in amino acid changes was evaluated to determine its somatic nature; of these, eight were found to be somatic and 19 were found in the germline of the same patient. Of the 13 variants in rRNA or tRNA genes, nine were evaluated in this way and four were found to be somatic. Twenty-five of the 48 silent mutations were also evaluated, and none of these were found to be somatic.

Of the 12 somatic mutations identified, eight were in protein encoding genes and four were in rRNA genes (Table 1). Eleven were nucleotide substitutions and one was a single bp insertion. Of the eight mutations in protein-encoding genes, one was a nonsense mutation, one was a 1-bp insertion, and six were missense mutations (Table 1). All but one of the 11 nt substitutions were T to C or G to A transitions. This mutational spectrum is fully consistent with the known mutagenic spectra of oxidative damage (12, 13).

To determine whether these mutations arose in vivo rather than during the process of cell culture, DNA was purified from five of the primary tumors from which the lines were derived (in two cases, no primary tumors were available). In every evaluable case, the mutation was found in the primary tumor as well as in the cell line (examples in FIG. 1).

Figure 1:
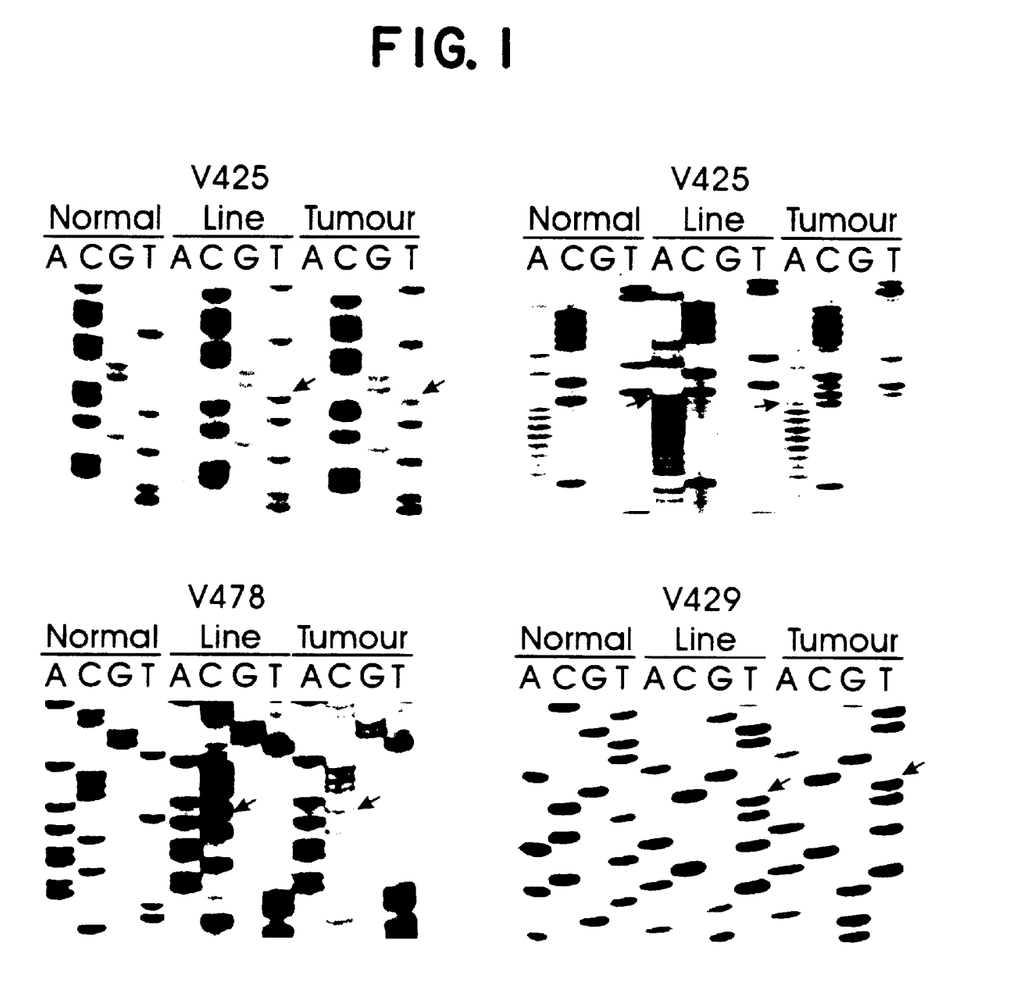

Surprisingly, each of the 12 mutations was present in a major portion of the mitochondrial DNA molecules, and in ten of the 12 cases, the mutations were homoplasmic, i.e., apparently present in every mitochondrial genome (Table 1). This homoplasmy was observed both in the primary tumors as well as in the cell lines (FIG. 1).

EXAMPLE 2

Proliferation of mitochondria harboring somatic mutations.

Cell fusion experiments have indicated that mitochondria from tumor cells can selectively proliferate when such cells are fused to normal cells (15). The inventors sought to determine whether a similar mitochondrial dominance could be observed upon fusion between two colorectal cancer cell lines. Attempts to fuse the lines studied for mitochondrial mutations were unsuccessful for technical reasons. Therefore, more commonly used colorectal cancer cell lines were employed in which intercellular fusions are possible (16).

Geneticin-resistant DLD-1 cells were fused to hygromycin-resistant subclones of each of three different colorectal cancer cell lines (HCT 116, HT29, and SW837). Geneticin- or hygromycin-resistant clones were derived through transfection of appropriate plasmid vectors. Approximately $10^6$ hygromycin-resistant cells were mixed with an equal number of neomycin-resistant cells and fused by PEG treatment as described (16). Hybrids were selected in standard growth medium containing 1 mg/ml geneticin and 0.25 mg/ml hygromycin (DLD-1-HCT116 fusion), 1.5 mg/ml geneticin and 0.6 mg/ml hygromycin (DLD-HT29 fusion) and 1 mg/ml geneticin and 0.25 mg/ml hygromycin (DLD-SW837 fusion). Successful fusions were verified by nuclear genotyping. Allelotyping was carried out as described (29) using the primer pair wg1g5A/wg1g5B or MapPair primers for D19S591 and D16S764 (Research Genetics). Amplified fragments were resolved by electrophoresis in 8% polyacrylamide gels. Reactions using radioactively labeled primers were separated on a 4.5% sequencing gel (Genomyx), while reactions using fluorescence labeled primers were analyzed on an ABI Sequencing System (Perkin-Elmer).

Figure 2A:
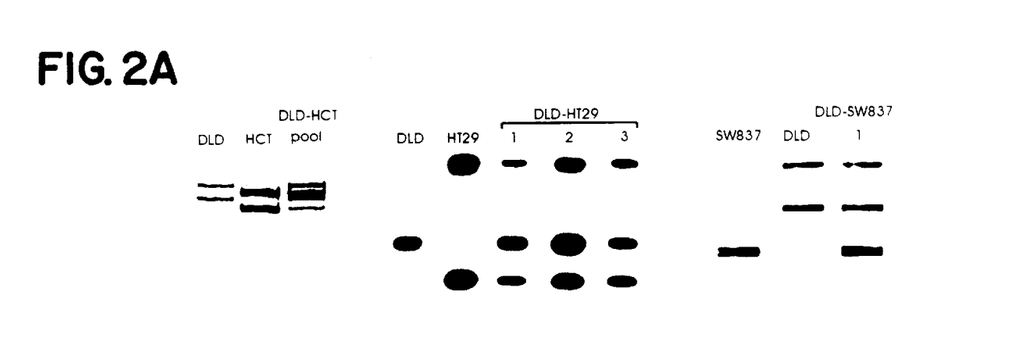
FIG. 2A. Confirmation of successful nuclear fusion using nuclear genomic DNA polymorphisms from the indicated lines.
Figure 2B:
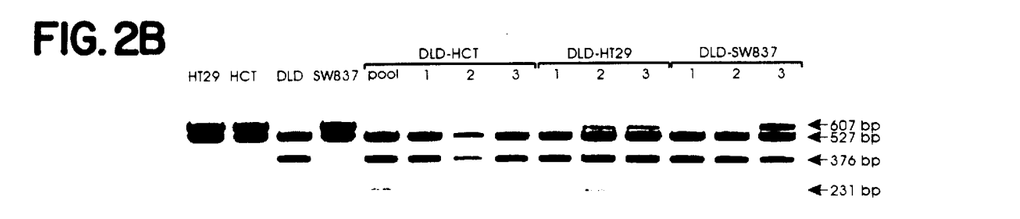
Figure 2C:
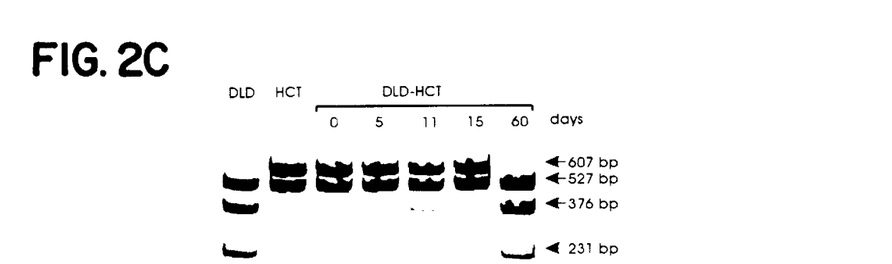
FIG. 2C. Time course over which replicative advantage of DLD-1 mitochondria is evident. Initially, HCT116 cell mitochondria were slightly over represented in the fusions, but a shift towards DLD-1 mitochondria was evident within five days and this process was complete between 15 and 60 days. DNA was isolated and the mitochondria were analyzed by Nla III digestion on the indicated days after cell fusion.

The success of fusion was demonstrated using nuclear genomic polymorphisms (FIG. 2A). Complete sequencing of the mitochondrial genomes revealed 3–7 potential variants in each line; it could not be determined which of these were somatic, as normal cells derived from the individuals from whom the cell lines were derived were not available. However, these variants provided a convenient method to trace the fate of the mitochondrial DNA in the fusions. In particular, a T to C variant at nucleotide 4,216 was used that creates a restriction endonuclease recognition site for Nla III (FIG. 2B). The C variant was present in DLD-1 cells but not in any of the other three lines. As shown in FIG. 2B, the DLD-1 mitochondria were "dominant" over the other mitochondria in each of the fusions. All three tested clones derived from DLD-1/HCT116 fusions contained mitochondria exclusively of DLD-1 origin. A pool of over 100 stable clones from this fusion also contained only mitochondria from DLD-1 cells. DLD-1 mitochondria were also dominant to those from HT29 and SW837 cells, contributing either all or the majority of mitochondrial genomes in the clones tested (FIG. 2B).

To determine the time course over which the replicative advantage of DLD1-1 mitochondria occurred, pooled clones from DLD-1/HCT116 fusions were followed. At the initiation of this experiment, there was a mixture of mitochondrial genomes, with a slight excess of the mitochondria from HCT116 cells. Within five days, a skewing towards DLD-1 mitochondria was evident, and a major shift occurred between 15 and 60 days after fusion, by which time only DLD-1 mitochondria remained in the hybrids (FIG. 2C). Whether it was strictly the mitochondria, or a combination of nuclear and mitochondrial factors, that was responsible for the selection of DLD-1 mitochondria could not be determined. However, these experiments clearly documented that tumor mitochondria of one type can have a significant replicative advantage over other types, and are consistent with other experiments documenting the potential for mitochondrial dominance (15).

REFERENCE

1. Warburg, O. On the origin of cancer cells. *Science* 123, 309–314(1956).
2. Kroemer, G., Zamzami, N. & Susin, S. A. Mitochondrial control of apoptosis. *Immun. Today* 18, 45–51(1997).
3. Korsmeyer, S. J., Yin, X. M., Oltvai, Z. N. Veis-Novack, D. J. & Linette, G. P. Reactive oxygen species and the regulation of cell death by the Bcl-2 gene family. *Biochim. Biophys. Acta* 1271, 63–66 (1995).
4. Rudin, C. M. & Thompson, C. B. Apoptosis and disease: regulation and clinical relevance of programmed cell death. *Annu. Rev. Med.* 48, 267–281 (1997).
5. Wang, H. G. & Reed, J. C. Mechanisms of Bcl-2 protein function. *Histol. Histopathol.* 13, 521–530 (1998).
6. Cavalli, L. R. & B. C., L. Mutagenesis, tumorigenicity, and apoptosis: are the mitochondria involved? *Muta. Res.* 398, 19–26 (1998).
7. Lightowlers R N, C. P., Turnbull D M, Howell N. Mammalian mitochondrial genetics: heredity, heteroplasmy and disease. *Trends Genet.* 13, 450–455 (1997).
8. Beal, M. Mitochondria, free radical, and neurodegeneration. *Curr. Opin. Neurobiol.* 6, 661–666 (1996).
9. Li, Y., Zhou, H., Stansbury, K. & Trush, M. Role of reactive oxygen species in multistage carcinogenesis. in *Oxygen radicals and the disease process* (eds. Thomas, C. & Kalyanaraman, B.) 237–277 (Harwood Academic Publishers, 1997).
10. Croteau, D. L. & Bohr, V. A. Repair of oxidative damage to nuclear and mitochondrial DNA in mammalian cells. *J. Biol. Chem.* 272, 25409–25412 (1997).
11. Parfait B. R. P., Munnich A, Rotig A. Co-amplification of nuclear pseudogenes and assessment of heteroplasmy of mitochondrial DNA mutations. *Biochem. Biophys. Res. Commun.* 247, 57–59 (1998).
12. Beckman, K. B. & Ames, B. N. Oxidative decay of DNA. J. Biol. Chem. 272, 19633–6 (1997).
13. Cadet, J., Berger, M. Douki, T. & Ravanat, J. L. Oxidative damage to DNA: formation measurement, and biological significance. *Rev. Physiol. Biochem. Pharmacol.* 131, 1–87 (1997).
14. Wallace, D. C., Brown, M. D., Melov, S., Graham, B. & Lott, M. Mitochondrial biology degenerative diseases and aging. *Biofactors* 7, 187–190 (1998).
15. Shay, J. & Ishii, S. Unexpected nonrandom mitochondrial DNA segregation in human cell hybrids. *Anticancer. Res.* 10, 279–284 (1990).
16. Lengauer, C., Kinzler, K. W. & Vogelstein, B. Genetic instability in colorectal cancers. *Nature* 386, 623–627 (1997).
17. Khrapko, K. et al. Mitochondrial mutational spectra in human cells and tissues. *Proc. Natl. Acad. Sci. U.S.A.* 94, 13798–13803 (1997).
18. Beckman, K. & Ames, B. Detection and guantification of oxidative adducts of mitochondrial DNA. *Methods Enzymol.* 264, 442–153 (1996).
19. Welter, C., Kovacs, G., Seitz, G. & Blin, N. Alteration of mitochondrial DNA in human oncocyomas. *Genes Chromosomes Cancer* 1, 79–82 (1989).
20. Yamamoto, H. et al. Significant existence of deleted mitochondrial DNA in cirrhotic liver surrounding hepatic tumor. Biochem. Biophys. Res. Commun. 182, 913–920 (1992).
21. Burgart, L. J. Zheng, J., Shu, Q., Strickler, J. G. & Shibata, D. Somatic mitochondrial mutation in gastric cancer. *Am. J. Pathol.* 147, 1105–1111 (1995).
22. Tallini, G. Ladanyi, M., Roasi, J. & Jhanwar, S. Analysis of nuclear and mitochondrial DNA alterations in thyroid and renal oncocytic tumour. *Cytogenet. Cell Genet.* 66, 253–259 (1994).
23. Heerdt, G. G., Chen, J., Stewart, L. R. & Augenlicht, L. H. Polymorphisms, but lack of mutations or instability, the promotor region of the mitochondrial genome in human colonic tumors. *Cancer Res.* 54, 3912–3915 (1994).
24. Wallace, D. C. Mitochondrial DNA sequence variation in human evolution and disease. *Proc Natl. Acad. Sci. U.S.A.* 91, 87–39–46 (1994).
25. Attardi, g., Yoneda, M. & Chomyn, A. Complementation and segregation behavior of disease-causing mitochondrial DNA mutation in cellular model systems. *Biochim. Biophys. Acta* 1271, 241–248 (1995).
26. Chee, M. et al. Accessing genetic information with high-density DNA arrays. *Science* 274, 610–614 (1996).
27. Parsons, R. et al. Microsatellite instability and mutations of the transforming growth factor beta type 11 Receptor gene in colorectal cancer. *Cancer Res.* 55, 5548–5550 (1995).
28. Jen, J. et al. Allelic loss of chromosome 18q and prognosis in colorectal cancer. *N. England. J. Med.* 331, 213–221 (1994).
29. Armour, J. A., Neumann, R., Gobert, S. & Jeffreys, A. J. Isolation of human simple repeat loci by hybridization selection. *Hum. Mol. Genet.* 3, 599–565 (1994).

TABLE 1

Summary of mtDNA mutations

| Tumor* | Position | DNA | Protein | Gene |
|---|---|---|---|---|
| V478 | 710 | T → C | — | 12S rRNA |
| " | 1738 | T → C | — | 16S rRNA |
| " | 3308 | T → C | M1T | ND1 |
| V429 | 8009 | G → A | V142M | COX subunit II |
| " | 14985 | G → A | R80H | CYT b |
| " | 15572 | T → C | F276L | CYT b |
| V441 | 9949 | G → A | V2481 | COX subunit III |
| V456 | 10563 | T → C | C32R | ND4L |
| V425 | 6264 | G → A | G121trun | COX subunit I |
| " | 12418 | insA | K28frameshift | ND5 |
| V451 | 1967 | T → C | — | 16S rRNA |
| V410 | 2299 | T → A | — | 16S rRNA |

*All the mutations were homoplasmic except V451 T11967C and V410 T2299A, which were present in ~50% of the mitochondrial DNA molecules.

We claim:

1. A method to aid in detecting the presence of tumor cells in a patient, comprising the steps of:

determining the presence of a single basepair mutation in a mitochondrial genome of a cell sample of a patient, wherein the mutation is found in a tumor of the patient but not in normal tissue of the patient; wherein the mutation is selected from the group consisting of a T→C substitution at position 710 according to SEQ ID NO: 1, a T→C substitution at position 1738 according to SEQ ID NO: 1, a T→C substitution at position 3308 according to SEQ ID NO: 1 a G→A substitution at position 8009 according to SEQ ID NO: 1, a G→A substitution at position 14985 according to SEQ ID NO: 1, a T→C substitution at position 15572 according to SEQ ID NO: 1, a G→A substitution at position 9949 according to SEQ ID NO: 1, a T→C substitution at position 10563 according to SEQ ID NO: 1, a G→A substitution at position 6264 according to SEQ ID NO: 1, an A insertion at position 12418 according to SEQ ID NO: 1, a T→C substitution at position 1967 according to SEQ ID NO: 1, and a T→A substitution at position 2299 according to SEQ ID NO: 1; and identifying the patient as having a tumor if one or more single basepair mutations are determined in the mitochondrial genome of the cell sample of the patient.

2. The method of claim 1 wherein the cell sample is from a tissue suspected of harboring a metastasis.

3. The method of claim 1 wherein the cell sample is from blood.

4. The method of claim 1 wherein the cell sample is from urine.

5. The method of claim 1 wherein the cell sample is from sputum.

6. The method of claim 1 wherein the cell sample is from saliva.

7. The method of claim 1 wherein the cell sample is from feces.

8. The method of claim 1 wherein the step of determining comprises amplifying mitochondrial DNA.

9. The method of claim 1 wherein the step of determining comprises sequencing mitochondrial DNA.

10. The method of claim 1 wherein the step of determining comprises hybridization of DNA amplified from the mitochondrial genome of the cell sample to an array of oligonucleotides which comprises matched and mismatched sequences to human mitochondrial genomic DNA.

11. The method of claim 1 wherein the single basepair mutation is a homoplasmic mutation selected from the group consisting of a T→C substitution at position 710 according to SEQ ID NO: 1, a T→C substitution at position 1738 according to SEQ ID NO: 1, a T→C substitution at position 3308 according to SEQ ID NO: 1, a G→A substitution at position 8009 according to SEQ ID NO: 1, a G→A substitution at position 14985 according to SEQ ID NO: 1, a T→C substitution at position 15572 according to SEQ ID NO: 1, a G→A substitution at position 9949 according to SEQ ID NO: 1, a T→C substitution at position 10563 according to SEQ ID NO: 1, a G→A substitution at position 6264 according to SEQ ID NO: 1, and an A insertion at position 12418 according to SEQ ID NO: 1.

12. The method of claim 1 wherein the single basepair mutation is a T→C substitution at position 710 according to SEQ ID NO: 1.

13. The method of claim 1 wherein the single basepair mutation is a T→C substitution at position 1738 according to SEQ ID NO: 1.

14. The method of claim 1 wherein the single basepair mutation is a T→C substitution at position 3308 according to SEQ ID NO: 1.

15. The method of claim 1 wherein the single basepair mutation is a G→A substitution at position 8009 according to SEQ ID NO: 1.

16. The method of claim 1 wherein the single basepair mutation is a G→A substitution at position 14985 according to SEQ ID NO: 1.

17. The method of claim 1 wherein the single basepair mutation is a T→C substitution at position 15572 according to SEQ ID NO: 1.

18. The method of claim 1 wherein the single basepair mutation is a G→A substitution at position 9949 according to SEQ ID NO: 1.

19. The method of claim 1 wherein the single basepair mutation is a T→C substitution at position 10563 according to SEQ ID NO: 1.

20. The method of claim 1 wherein the single basepair mutation is a G→A substitution at position 6264 according to SEQ ID NO: 1.

21. The method of claim 1 wherein the single basepair mutation is an A insertion at position 12418 according to SEQ ID NO: 1.

22. The method of claim 1 wherein the single basepair mutation is a T→C substitution at position 1967 according to SEQ ID NO: 1.

23. The method of claim 1 wherein the single basepair mutation is a T→A substitution at position 2299 according to SEQ ID NO: 1.

24. The method of claim 1 wherein the mutation was identified previously in a tumor of the patient.

25. The method of claim 24 wherein the patient has received anti-cancer therapy and the step of determining is performed at least three times to monitor progress of the anti-cancer therapy.

26. The method of claim 1 further comprising the step of testing a normal tissue of the patient to determine the absence of the mutation.

27. The method of claim 1 wherein the cell sample is from a tumor.

* * * * *

SEQUENCE LISTING

```
<160> NUMBER OF SEQ ID NOS:  1

<210> SEQ ID NO 1
<211> LENGTH: 16569
<212> TYPE: DNA
<213> ORGANISM: Homo sapiens

<400> SEQUENCE: 1
gatcacaggt ctatcaccct attaaccact cacgggagct ctccatgcat ttggtatttt      60
cgtctggggg gtatgcacgc gatagcattg cgagacgctg gagccggagc accctatgtc     120
gcagtatctg tctttgattc ctgcctcatc ctattattta tcgcacctac gttcaatatt     180
acaggcgaac atacttacta aagtgtgtta attaattaat gcttgtagga cataataata     240
acaattgaat gtctgcacag ccactttcca cacagacatc ataacaaaaa atttccacca     300
```

-continued

```
aaccccccct cccccgcttc tggccacagc acttaaacac atctctgcca aaccccaaaa      360
acaaagaacc ctaacaccag cctaaccaga tttcaaattt tatcttttgg cggtatgcac      420
ttttaacagt cacccccaa  ctaacacatt attttcccct cccactccca tactactaat      480
ctcatcaata caaccccgc  ccatcctacc cagcacacac acaccgctgc taaccccata      540
ccccgaacca accaaacccc aaagacaccc cccacagttt atgtagctta cctcctcaaa      600
gcaatacact gaaaatgttt agacgggctc acatcacccc ataaacaaat aggtttggtc      660 ctagccttc  tattagctct tagtaagatt acacatgcaa gcatcccgt tccagtgagt       720 tcaccctcta aatcaccacg atcaaaaggg acaagcatca agcacgcagc aatgcagctc      780
aaaacgctta gcctagccac accccacgg  gaaacagcag tgattaacct ttagcaataa      840
acgaaagttt aactaagcta tactaacccc agggttggtc aatttcgtgc cagccaccgc      900
ggtcacacga ttaacccaag tcaatagaag ccggcgtaaa gagtgtttta gatcacccc      960 tccccaataa agctaaaact cacctgagtt gtaaaaaact ccagttgaca caaaatagac     1020
tacgaaagtg gctttaacat atctgaacac acaatagcta agaccaaac  tgggattaga     1080 taccccacta tgcttagccc taaacctcaa cagttaaatc aacaaaactg ctcgccagaa     1140
cactacgagc cacagcttaa aactcaaagg acctggcggt gcttcatatc cctctagagg     1200
agcctgttct gtaatcgata aaccccgatc aacctcacca cctcttgctc agcctatata     1260
ccgccatctt cagcaaaccc tgatgaaggc tacaaagtaa gcgcaagtac ccacgtaaag     1320
acgttaggtc aaggtgtagc ccatgagtg  gcaagaaatg ggctacattt tctacccag      1380 aaaactacga tagcccttat gaaacttaag ggtcgaaggt ggatttagca gtaaactaag     1440
agtagagtgc ttagttgaac agggccctga agcgcgtaca caccgcccgt cacccctcctc    1500 aagtatactt caaggacat  ttaactaaaa cccctacgca tttatataga ggagacaagt     1560
cgtaacatgg taagtgtact ggaaagtgca cttggacgaa ccagagtgta gcttaacaca     1620
aagcacccaa cttacactta ggagatttca acttaacttg accgctctga gctaaaccta     1680
gccccaaacc cactccacct tactaccaga caaccttagc caaaccattt acccaaataa     1740
agtataggcg atagaaattg aaacctggcg caatagatat agtaccgcaa gggaaagatg     1800
aaaaattata accaagcata atatagcaag gactaacccc tataccttct gcataatgaa     1860
ttaactagaa ataactttgc aaggagagcc aaagctaaga cccccgaaac cagacgagct     1920
acctaagaac agctaaaaga gcacacccgt ctatgtagca aaatagtggg aagatttata     1980
ggtagaggcg acaaacctac cgagcctggt gatagctggt tgtccaagat agaatcttag     2040
ttcaacttta aatttgccca cagaaccctc taaatcccct tgtaaattta actgttagtc     2100
caaagaggaa cagctctttg gacactagga aaaaccttg  tagagagagt aaaaaattta     2160
acacccatag taggcctaaa agcagccacc aattaagaaa gcgttcaagc tcaacaccca     2220
ctacctaaaa aatcccaaac atataactga actcctcaca cccaattgga ccaatctatc     2280 acctataga  agaactaatg ttagtataag taacatgaaa acattctcct ccgcataagc     2340
ctgcgtcaga ttaaacact  gaactgacaa ttaacagccc aatatctaca atcaaccaac     2400
aagtcattat taccctcact gtcaacccaa cacaggcatg ctcataagga aaggttaaaa     2460
aaagtaaaag gaactcggca aatcttaccc cgcctgttta ccaaaaacat cacctctagc     2520
atcaccagta ttagaggcac cgcctgccca gtgacacatg tttaacggcc gcggtacccct   2580 aaccgtgcaa aggtagcata atcacttgtt ccttaaatag ggacctgtat gaatggctcc     2640
acgagggttc agctgtctct tacttttaac cagtgaaatt gacctgcccg tgaagaggcg     2700
```

-continued

```
ggcataacac agcaagacga gaagaccota tggagcttta atttattaat gcaaacagta    2760
cctaacaaac ccacaggtcc taaactacca aacctgcatt aaaaatttcg gttggggcga    2820
cctcggagca gaacccaacc tccgagcagt acatgctaag acttcaccag tcaaagcgaa    2880
ctactatact caattgatcc aataacttga ccaacggaac aagttaccct agggataaca    2940
gcgcaatcct attctagagt ccatatcaac aatagggttt acgacctcga tgttggatca    3000
ggacatcccg atggtgcagc cgctattaaa ggttcgtttg ttcaacgatt aaagtcctac    3060
gtgatctgag ttcagaccgg agtaatccag gtcggtttct atctaccttc aaattcctcc    3120
ctgtacgaaa ggacaagaga aataaggcct acttcacaaa gcgccttccc ccgtaaatga    3180
tatcatctca acttagtatt atacccacac ccacccaaga acagggtttg ttaagatggc    3240
agagcccggt aatcgcataa aacttaaaac tttacagtca gaggttcaat tcctcttctt    3300
aacaacatac ccatggccaa cctcctactc ctcattgtac ccattctaat cgcaatggca    3360
ttcctaatgc ttaccgaacg aaaaattcta ggctatatac aactacgcaa aggccccaac    3420
gttgtaggcc cctacgggct actacaaccc ttcgctgacg ccataaaact cttcaccaaa    3480
gagcccctaa aacccgccac atctaccatc accctctaca tcaccgcccc gaccttagct    3540
ctcaccatcg ctcttctact atgaaccccc ctccccatac caacccccct ggtcaacctc    3600
aacctaggcc tcctatttat tctagccacc tctagcctag ccgtttactc aatcctctga    3660
tcagggtgag catcaaactc aaactacgcc ctgatcggcg cactgcgagc agtagcccaa    3720
acaatctcat atgaagtcac cctagccatc attctactat caacattact aataagtggc    3780
tcctttaacc tctccaccct tatcacaaca caagaacacc tctgattact cctgccatca    3840
tgacccttgg ccataatatg atttatctcc acactagcag agaccaaccg aacccccttc    3900
gaccttgccg aagggagtc cgaactagtc tcaggcttca acatcgaata cgccgcaggc    3960
cccttcgccc tattcttcat agccgaatac acaaacatta ttaataaaa ccccctcacc    4020
actacaatct tcctaggaac aacatatgac gcactctccc ctgaactcta cacaacatat    4080
tttgtcacca agaccctact tctaacctcc ctgttcttat gaattcgaac agcatacccc    4140
cgattccgct acgaccaact catacacctc ctatgaaaaa acttcctacc actcacccta    4200
gcattactta tatgatatgt ctccataccc attacaatct ccagcattcc ccctcaaacc    4260
taagaaatat gtctgataaa agagttactt tgatagagta aataatagga gcttaaaccc    4320
ccttatttct aggactatga gaatcgaacc catccctgag aatccaaaat tctccgtgcc    4380
acctatcaca ccccatccta agtaaggtc agctaaataa gctatcgggc ccataccccg    4440
aaaatgttgg ttatacccct tccgtactaa ttaatcccct ggcccaaccc gtcatctact    4500
ctaccatctt tgcaggcaca ctcatcacag cgctaagctc gcactgattt tttacctgag    4560
taggcctaga aataaacatg ctagctttta ttccagttct aaccaaaaaa ataaaccctc    4620
gttccacaga agctgccatc aagtatttcc tcacgcaagc aaccgcatcc ataatccttc    4680
taatagctat cctcttcaac aatatactct ccggacaatg aaccataacc aatactacca    4740
atcaatactc atcattaata atcataatag ctatagcaat aaaactagga atagccccct    4800
ttcacttctg agtcccagag gttacccaag gcacccctct gacatccggc ctgcttcttc    4860
tcacatgaca aaaactagcc cccatctcaa tcatatacca aatctctccc tcactaaacg    4920
taagccttct cctcactctc tcaatcttat ccatcatagc aggcagttga ggtggattaa    4980
accagaccca gctacgcaaa atcttagcat actcctcaat tacccacata ggatgaataa    5040
tagcagttct accgtacaac cctaacataa ccattcttaa tttaactatt tatattatcc    5100
```

-continued

```
taactactac cgcattccta ctactcaact taaactccag caccacgacc ctactactat    5160
ctcgcacctg aaacaagcta acatgactaa caccettaat tccatccacc ctcctctccc    5220
taggaggcct gccccgcta accggctttt tgcccaaatg ggccattatc gaagaattca     5280
caaaaaacaa tagcctcatc atccccacca tcatagccac catcaccctc cttaacctct    5340
acttctacct acgcctaatc tactccacct caatcacact actccccata tctaacaacg    5400
taaaaataaa atgacagttt gaacatacaa acccaccc attcctcccc acactcatcg      5460
cccttaccac gctactccta cctatctccc cttttatact aataatctta tagaaattta    5520
ggttaaatac agaccaagag ccttcaaagc cctcagtaag ttgcaatact taatttctgt    5580
aacagctaag gactgcaaaa ccccactctg catcaactga acgcaaatca gccactttaa    5640
ttaagctaag cccttactag accaatggga cttaaaccca caaacactta gttaacagct    5700
aagcacccta atcaactggc ttcaatctac ttctcccgcc gccgggaaaa aaggcgggag    5760
aagccccggc aggtttgaag ctgcttcttc gaatttgcaa ttcaatatga aaatcacctc    5820
ggagctggta aaaagaggcc taaccccgt ctttagattt acagtccaat gcttcactca    5880
gccattttac ctcaccccca ctgatgttcg ccgaccgttg actattctct acaaaccaca    5940
aagacattgg aacactatac ctattattcg gcgcatgagc tggagtccta ggcacagctc    6000
taagcctcct tattcgagcc gagctgggcc agccaggcaa ccttctaggt aacgaccaca    6060
tctacaacgt tatcgtcaca gcccatgcat ttgtaataat cttcttcata gtaatacca    6120 tcataatcgg aggctttggc aactgactag ttcccctaat aatcggtgcc cccgatatgg    6180 cgtttcccg cataaacaac ataagcttct gactcttacc tccctctctc ctactcctgc    6240
tcgcatctgc tatagtggag gccggagcag gaacaggttg aacagtctac cctcccttag    6300
cagggaacta ctcccaccct ggagcctccg tagacctaac catcttctcc ttacacctag    6360
caggtgtctc ctctatctta ggggccatca atttcatcac aacaattatc aatataaaac    6420
cccctgccat aacccaatac caaacgcccc tcttcgtctg atccgtccta atcacagcag    6480
tcctacttct cctatctctc ccagtcctag ctgctggcat cactatacta ctaacagacc    6540
gcaacctcaa caccaccttc ttcgaccccg ccggaggagg agaccccatt ctataccaac    6600
acctattctg atttttcggt caccctgaag tttatattct tatcctacca ggcttcggaa    6660
taatctccca tattgtaact tactactccg aaaaaaaga accatttgga tacataggta    6720
tggtctgagc tatgatatca attggcttcc tagggtttat cgtgtgagca caccatatat    6780
ttacagtagg aatagacgta gacacacgag catatttcac ctccgctacc ataatcatcg    6840
ctatccccac cggcgtcaaa gtatttagct gactcgccac actccacgga agcaatatga    6900
aatgatctgc tgcagtgctc tgagccctag gattcatctt tcttttcacc gtaggtggcc    6960
tgactggcat tgtattagca aactcatcac tagacatcgt actacacgac acgtactacg    7020
ttgtagccca cttccactat gtcctatcaa taggagctgt atttgccatc ataggaggct    7080
tcattcactg atttccccta ttctcaggct acaccctaga ccaaacctac gccaaaatcc    7140
atttcactat catattcatc ggcgtaaatc taactttctt cccacaacac tttctcggcc    7200
tatccggaat gccccgacgt tactcggact acccgatgc atacaccaca tgaaacatcc    7260
tatcatctgt aggctcattc atttctctaa cagcagtaat attaataatt ttcatgattt    7320
gagaagcctt cgcttcgaag cgaaaagtcc taatagtaga agaaccctcc ataaacctgg    7380
agtgactata tggatgcccc ccacccctacc acacattcga agaacccgta tacataaaat    7440
ctagacaaaa aaggaaggaa tcgaacccc caaagctggt ttcaagccaa ccccatggcc    7500
```

-continued

```
tccatgactt tttcaaaaag gtattagaaa aaccatttca taactttgtc aaagttaaat    7560
tataggctaa atcctatata tcttaatggc acatgcagcg caagtaggtc tacaagacgc    7620
tacttcccct atcatagaag agcttatcac ctttcatgat cacgccctca taatcatttt    7680
ccttatctgc ttcctagtcc tgtatgccct tttcctaaca ctcacaacaa actaactaa    7740
tactaacatc tcagacgctc aggaaataga aaccgtctga actatcctgc ccgccatcat    7800
cctagtcctc atcgccctcc catccctacg catcctttac ataacagacg aggtcaacga    7860
tccctccctt accatcaaat caattggcca ccaatggtac tgaacctacg agtacaccga    7920
ctacggcgga ctaatcttca actcctacat acttccccca ttattcctag aaccaggcga    7980
cctgcgactc cttgacgttg acaatcgagt agtactcccg attgaagccc ccattcgtat    8040
aataattaca tcacaagacg tcttgcactc atgagctgtc cccacattag gcttaaaaac    8100
agatgcaatt cccggacgtc taaaccaaac cactttcacc gctacacgac cgggggtata    8160
ctacggtcaa tgctctgaaa tctgtggagc aaaccacagt ttcatgccca tcgtcctaga    8220
attaattccc ctaaaaatct ttgaaatagg gcccgtattt accctatagc accccctcta    8280
cccctctag agcccactgt aaagctaact tagcattaac cttttaagtt aaagattaag    8340
agaaccaaca cctctttaca gtgaaatgcc ccaactaaat actaccgtat ggcccaccat    8400
aattacccc atactcctta cactattcct catcacccaa ctaaaaatat taaacacaaa    8460
ctaccaccta cctccctcac caaagcccat aaaaataaaa aattataaca aaccctgaga    8520
accaaaatga acgaaaatct gttcgcttca ttcattgccc ccacaatcct aggcctaccc    8580
gccgcagtac tgatcattct atttcccct ctattgatcc ccacctccaa atatctcatc    8640
aacaaccgac taatcaccac ccaacaatga ctaatcaaac taacctcaaa acaaatgata    8700
accatacaca cactaaagg acgaacctga tctcttatac tagtatcctt aatcattttt    8760
attgccacaa ctaacctcct cggactcctg cctcactcat ttacaccaac cacccaacta    8820
tctataaacc tagccatggc catcccctta tgagcgggca cagtgattat aggctttcgc    8880
tctaagatta aaaatgccct agcccacttc ttaccacaag gcacacctac ccccttatc    8940
cccatactag ttattatcga aaccatcagc ctactcattc aaccaatagc cctggccgta    9000
cgcctaaccg ctaacattac tgcaggccac ctactcatgc acctaattgg aagcgccacc    9060
ctagcaatat caaccattaa ccttccctct acacttatca tcttcacaat tctaattcta    9120
ctgactatcc tagaaatcgc tgtcgcctta atccaagcct acgttttcac acttctagta    9180
agcctctacc tgcacgacaa cacataatga cccaccaatc acatgcctat catatagtaa    9240
aacccagccc atgacccta acaggggccc tctcagccct cctaatgacc tccggcctag    9300
ccatgtgatt tcacttccac tccataacgc tcctcatact aggcctacta accaacacac    9360
taaccatata ccaatgatgg cgcgatgtaa cacgagaaag cacataccaa ggccaccaca    9420
caccacctgt ccaaaaaggc cttcgatacg ggataatcct atttattacc tcagaagttt    9480
ttttcttcgc aggatttttc tgagcctttt accactccag cctagcccct accccccaat    9540
taggagggca ctggccccca acaggcatca cccgctaaa tccctagaa gtcccactcc    9600
taaacacatc cgtattactc gcatcaggag tatcaatcac ctgagctcac catagtctaa    9660
tagaaaacaa ccgaaaccaa ataattcaag cactgcttat tacaattta ctgggtctct    9720
attttaccct cctacaagcc tcagagtact tcgagtctcc cttcaccatt tccgacggca    9780
tctacggctc aacattttt gtagccacag gcttccacgg acttcacgtc attattggct    9840
caactttcct cactatctgc ttcatccgcc aactaatatt tcactttaca tccaaacatc    9900
```

```
actttggctt cgaagccgcc gcctgatact ggcattttgt agatgtggtt tgactatttc    9960
tgtatgtctc catctattga tgagggtctt actcttttag tataaatagt accgttaact   10020
tccaattaac tagttttgac aacattcaaa aagagtaat aaacttcgcc ttaattttaa   10080
taatcaacac cctcctagcc ttactactaa taattattac attttgacta ccacaactca   10140
acggctacat agaaaaatcc accccttacg agtgcggctt cgaccctata tccccgccc    10200
gcgtcccttt ctccataaaa ttcttcttag tagctattac cttcttatta tttgatctag   10260
aaattgccct ccttttaccc ctaccatgag ccctacaaac aactaacctg ccactaatag   10320
ttatgtcatc cctcttatta atcatcatcc tagccctaag tctggcctat gagtgactac   10380
aaaaaggatt agactgaacc gaattggtat atagtttaaa caaaacgaat gatttcgact   10440
cattaaatta tgataatcat atttaccaaa tgcccctcat ttacataaat attatactag   10500
catttaccat ctcacttcta ggaatactag tatatcgctc acacctcata tcctccctac   10560
tatgcctaga aggaataata ctatcgctgt tcattatagc tactctcata accctcaaca   10620
cccactccct cttagccaat attgtgccta ttgccatact agtctttgcc gcctgcgaag   10680
cagcggtggg cctagcccta ctagtctcaa tctccaacac atatggccta gactacgtac   10740
ataacctaaa cctactccaa tgctaaaact aatcgtccca acaattatat tactaccact   10800
gacatgactt ccaaaaaac acataatttg aatcaacaca accacccaca gcctaattat   10860
tagcatcatc cctctactat ttttaacca aatcaacaac aacctattta gctgttcccc   10920
aaccttttcc tccgaccccc taacaacccc cctcctaata ctaactacct gactcctacc   10980
cctcacaatc atggcaagcc aacgccactt atccagtgaa ccactatcac gaaaaaact   11040
ctacctctct atactaatct ccctacaaat ctccttaatt ataacattca cagccacaga   11100
actaatcata ttttatatct tcttcgaaac cacacttatc cccaccttgg ctatcatcac   11160
ccgatgaggc aaccagccag aacgcctgaa cgcaggcaca tacttcctat tctacaccct   11220
agtaggctcc cttcccctac tcatcgcact aatttacact cacaacaccc taggctcact   11280
aaacattcta ctactcactc tcactgccca agaactatca aactcctgag ccaataactt   11340
aatatgacta gcttacacaa tagctttat agtaaagata cctctttacg gactccactt   11400
atgactccct aaagcccatg tcgaagcccc catcgctggg tcaatagtac ttgccgcagt   11460
actcttaaaa ctaggcggct atggtataat acgcctcaca ctcattctca accccctgac   11520
aaaacacata gcctacccct tccttgtact atccctatga ggcataatta taacaagctc   11580
catctgccta cgacaaacag acctaaaatc gctcattgca tactcttcaa tcagccacat   11640
agccctcgta gtaacagcca ttctcatcca accccctga agcttcaccg gcgcagtcat   11700
tctcataatc gcccacgggc ttacatcctc attactattc tgcctagcaa actcaaacta   11760
cgaacgcact cacagtcgca tcataatcct ctctcaagga cttcaaactc tactcccact   11820
aatagctttt tgatgacttc tagcaagcct cgctaacctc gccttacccc ccactattaa   11880
cctactggga gaactctctg tgctagtaac cacgttctcc tgatcaaata tcactctcct   11940
acttacagga ctcaacatac tagtcacagc cctatactcc ctctacatat ttaccacaac   12000
acaatgggc tcactcaccc accacattaa caacataaaa ccctcattca cacgagaaaa   12060
caccctcatg ttcatacacc tatcccccat tctcctccta tccctcaacc ccgacatcat   12120
taccgggttt tcctcttgta aatatagttt aaccaaaaca tcagattgtg aatctgacaa   12180
cagaggctta cgacccctta tttaccgaga aagctcacaa gaactgctaa ctcatgcccc   12240
catgtctaac aacatggctt tctcaacttt taaaggataa cagctatcca ttggtcttag   12300
```

-continued

```
gccccaaaaa ttttggtgca actccaaata aaagtaataa ccatgcacac tactataacc   12360
accctaaccc tgacttccct aattccccc  atccttacca ccctcgttaa ccctaacaaa   12420
aaaaactcat acccccatta tgtaaaatcc attgtcgcat ccacctttat tatcagtctc   12480
ttccccacaa caatattcat gtgcctagac caagaagtta ttatctcgaa ctgacactga   12540
gccacaaccc aaacaaccca gctctcccta agcttcaaac tagactactt ctccataata   12600
ttcatccctg tagcattgtt cgttacatgg tccatcatag aattctcact gtgatatata   12660
aactcagacc caaacattaa tcagttcttc aaatatctac tcatcttcct aattaccata   12720
ctaatcttag ttaccgctaa caacctattc caactgttca tcggctgaga gggcgtagga   12780
attatatcct tcttgctcat cagttgatga tacgcccgag cagatgccaa cacagcagcc   12840
attcaagcaa tcctatacaa ccgtatcggc gatatcggtt tcatcctcgc cttagcatga   12900
tttatcctac actccaactc atgagaccca caacaaatag cccttctaaa cgctaatcca   12960
agcctcaccc cactactagg cctcctccta gcagcagcag gcaaatcagc ccaattaggt   13020
ctccacccct gactcccctc agccatagaa ggccccaccc cagtctcagc cctactccac   13080
tcaagcacta tagttgtagc aggaatcttc ttactcatcc gcttccaccc cctagcagaa   13140
aatagcccac taatccaaac tctaacacta tgcttaggcg ctatcaccac tctgttcgca   13200
gcagtctgcg cccttacaca aaatgacatc aaaaaaatcg tagccttctc cacttcaagt   13260
caactaggac tcataatagt tacaatcggc atcaaccaac cacacctagc attcctgcac   13320
atctgtaccc acgccttctt caaagccata ctatttatgt gctccgggtc catcatccac   13380
aaccttaaca atgaacaaga tattcgaaaa ataggaggac tactcaaaac catacctctc   13440
acttcaacct ccctcaccat tggcagccta gcattagcag gaataccttt cctcacaggt   13500
ttctactcca aagaccacat catcgaaacc gcaaacatat catacacaaa cgcctgagcc   13560
ctatctatta ctctcatcgc tacctccctg acaagcgcct atagcactcg aataattctt   13620
ctcaccctaa caggtcaacc tcgcttcccc accttactaa acattaacga aaataacccc   13680
accctactaa accccattaa acgcctggca gccggaagcc tattcgcagg atttctcatt   13740
actaacaaca tttccccgc  atccccttc  caaacaacaa tccccctcta cctaaaactc   13800
acagccctcg ctgtcacttt cctaggactt ctaacagccc tagacctcaa ctacctaacc   13860
aacaaactta aaataaaatc cccactatgc acatttttatt tctccaacat actcggattc   13920
taccctagca tcacacaccg cacaatcccc tatctaggcc ttcttacgag ccaaaacctg   13980
cccctactcc tcctagacct aacctgacta gaaaagctat tacctaaaac aatttcacag   14040
caccaaatct ccacctccat catcacctca acccaaaaag gcataattaa actttacttc   14100
ctctctttct tcttcccact catcctaacc ctactcctaa tcacataacc tattccccg    14160 agcaatctca attacaatat atacaccaac aaacaatgtt caaccagtaa ctactactaa   14220
tcaacgccca taatcataca aagcccccgc accaatagga tcctcccgaa tcaaccctga   14280
cccctctcct tcataaatta ttcagcttcc tacactatta agtttacca  caaccaccac   14340 cccatcatac tctttcaccc acagcaccaa tcctacctcc atcgctaacc ccactaaaac   14400
actcaccaag acctcaaccc ctgaccccca tgcctcagga tactcctcaa tagccatcgc   14460
tgtagtatat ccaaagacaa ccatcattcc ccctaaataa attaaaaaaa ctattaaacc   14520
catataacct ccccccaaaat tcagaataat aacacacccg accacaccgc taacaatcaa   14580
tactaaaccc ccataaatag gagaaggctt agaagaaaac cccacaaacc ccattactaa   14640
acccacactc aacagaaaca aagcatacat cattattctc gcacggacta caaccacgac   14700
```

```
caatgatatg aaaaaccatc gttgtatttc aactacaaga acaccaatga ccccaatacg    14760
caaaattaac cccctaataa aattaattaa ccactcattc atcgacctcc ccaccccatc    14820
caacatctcc gcatgatgaa acttcggctc actccttggc gcctgcctga tcctccaaat    14880
caccacagga ctattcctag ccatgcacta ctcaccagac gcctcaaccg cctttcatc     14940 aatcgcccac atcactcgag acgtaaatta tggctgaatc atccgctacc ttcacgccaa    15000
tggcgcctca atattcttta tctgcctctt cctacacatc gggcgaggcc tatattacgg    15060
atcatttctc tactcagaaa cctgaaacat cggcattatc ctcctgcttg caactatagc    15120
aacagccttc ataggctatg tcctcccgtg aggccaaata tcattctgag gggccacagt    15180
aattacaaac ttactatccg ccatcccata cattgggaca gacctagttc aatgaatctg    15240
aggaggctac tcagtagaca gtcccaccct cacacgattc tttacctttc acttcatctt    15300
gcccttcatt attgcagccc tagcaacact ccacctccta ttcttgcacg aaacgggatc    15360
aaacaacccc ctaggaatca cctcccattc cgataaaatc accttccacc cttactacac    15420
aatcaaagac gccctcggct tacttctctt ccttctctcc ttaatgacat taacactatt    15480
ctcaccagac ctcctaggcg acccagacaa ttataccta gccaacccct aaacaccccc     15540
tccccacatc aagcccgaat gatatttcct attcgcctac acaattctcc gatccgtccc    15600
taacaaacta ggaggcgtcc ttgccctatt actatccatc ctcatcctag caataatccc    15660
catcctccat atatccaaac aacaaagcat aatatttcgc ccactaagcc aatcacttta    15720
ttgactccta gccgcagacc tcctcattct aacctgaatc ggaggacaac cagtaagcta    15780 ccctttacc atcattggac aagtagcatc cgtactatac ttcacaacaa tcctaatcct    15840
aataccaact atctccctaa ttgaaaacaa aatactcaaa tgggcctgtc cttgtagtat    15900
aaactaatac accagtcttg taaccggag atgaaaacct ttttccaagg acaaatcaga     15960 gaaaagtct ttaactccac cattagcacc caaagctaag attctaattt aaactattct     16020
ctgttctttc atggggaagc agatttgggt accaccaag tattgactca cccatcaaca     16080
accgctatgt atttcgtaca ttactgccag ccaccatgaa tattgtacgg taccataaat    16140
acttgaccac ctgtagtaca taaaaaccca atccacatca aaaccccctc cccatgctta    16200
caagcaagta cagcaatcaa ccctcaacta tcacacatca actgcaactc caaagccacc    16260
cctcacccac taggatacca acaaacctac ccaccttaa cagtacatag tacataaagc     16320
catttaccgt acatagcaca ttacagtcaa atcccttctc gtccccatgg atgacccccc    16380
tcagataggg gtcccttgac caccatcctc cgtgaaatca atatcccgca caagagtgct    16440
actctcctcg ctccgggccc ataacacttg ggggtagcta aagtgaactg tatccgacat    16500
ctggttccta cttcagggtc ataaagccta aatagcccac acgttcccct taaataagac    16560
atcacgatg                                                            16569
```